(12) United States Patent
Hively (10) Patent No.: US 7,209,861 B2
(45) Date of Patent: Apr. 24, 2007

(54) METHODS FOR IMPROVED FOREWARNING OF CRITICAL EVENTS ACROSS MULTIPLE DATA CHANNELS

(75) Inventor: Lee M. Hively, Philadelphia, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 492 days.

(21) Appl. No.: 10/667,045

(22) Filed: Sep. 22, 2003

(65) Prior Publication Data

US 2004/0059761 A1 Mar. 25, 2004

Related U.S. Application Data

(63) Continuation-in-part of application No. 10/195,626, filed on Jul. 12, 2002, now Pat. No. 7,139,677.

(51) Int. Cl.
*G06F 7/02* (2006.01)
(52) U.S. Cl. .................. 702/183; 702/182; 702/19
(58) Field of Classification Search ............ 702/183, 702/92, 22, 182; 600/300, 544, 545
See application file for complete search history.

(56) References Cited

U.S. PATENT DOCUMENTS

| | | | |
|---|---|---|---|
| 5,626,145 A * | 5/1997 | Clapp et al. ............ | 600/544 |
| 5,743,860 A | 4/1998 | Hively et al. | |
| 5,815,413 A * | 9/1998 | Hively et al. ............ | 702/191 |
| 5,857,978 A | 1/1999 | Hively et al. | |
| 6,484,132 B1 * | 11/2002 | Hively et al. ............ | 702/190 |

OTHER PUBLICATIONS

"Reconstructing embedding spaces of coupled dynamical systems from multivariate data", S. Boccaletti et al., The American Physical Society, Physical Review E, vol. 65 035204-1, published Feb. 21, 2002.

* cited by examiner

*Primary Examiner*—Manuel L. Barbee
(74) *Attorney, Agent, or Firm*—Quarles & Brady LLP (57) ABSTRACT

This disclosed invention concerns improvements in forewarning of critical events via phase-space dissimilarity analysis of data from mechanical devices, electrical devices, biomedical data, and other physical processes. First, a single channel of process-indicative data is selected that can be used in place of multiple data channels without sacrificing consistent forewarning of critical events. Second, the method discards data of inadequate quality via statistical analysis of the raw data, because the analysis of poor quality data always yields inferior results. Third, two separate filtering operations are used in sequence to remove both high-frequency and low-frequency artifacts using a zero-phase quadratic filter. Fourth, the method constructs phase-space dissimilarity measures (PSDM) by combining of multi-channel time-serial data into a multi-channel time-delay phase-space reconstruction. Fifth, the method uses a composite measure of dissimilarity ($C_i$) to provide a forewarning of failure and an indicator of failure onset.

18 Claims, 9 Drawing Sheets

TIME (ms)

METHODS FOR IMPROVED FOREWARNING OF CRITICAL EVENTS ACROSS MULTIPLE DATA CHANNELS

CROSS-REFERENCE TO RELATED APPLICATION

This is a continuation-in-part of Hively, U.S. patent application Ser. No. 10/195,626 filed Jul. 12, 2002 now U.S. Pat. No. 7,139,677.

STATEMENT REGARDING FEDERALLY SPONSORED RESEARCH

This invention was made with assistance under Contract No. DE-AC05-00OR22725 with the U.S. Department of Energy. The Government has certain rights in this invention.

BACKGROUND OF THE INVENTION

The field of the invention is computer methods for analyzing nonlinear processes to forewarn of critical events in nonlinear processes Examples of critical events are mechanical or electrical failures in machines; epileptic seizures, ventricular fibrillations, fainting (syncope), breathing difficulty, and sepsis in human medical patients; and other physical processes. Further examples of nonlinear processes include brain waves, heart waves, chest sounds, transients in power systems, airflow over automobiles and airplanes, weather and climate dynamics, water flow around submarines, machine tool-part interaction (e.g., tool chatter), nuclear reactor instabilities, fusion plasma instabilities, earthquakes, turbulent flow in pipes, planetary/satellite motion.

Engineering, medical, and research applications frequently must distinguish a difference between two apparently similar but actually different states in a nonlinear process. Examples include various data for machine failure, pre-seizure versus non-seizure brain waves, pre-fibrillation versus fibrillation heart waves, pre-syncope versus syncope heart waves, pre-sepsis versus sepsis heart waves, and normal versus abnormal chest sounds as an indicator of breathing difficulty. The electrical/mechanical community calls this problem, "condition monitoring." The equivalent term in the medical community is diagnostic, medical, or health monitoring. In the computer/networking world, the term is "security monitoring."

Hively et al., U.S. Pat. Nos. 5,743,860 and 5,857,978 disclose methods for detecting and predicting epileptic seizures by acquiring brain wave data from a patient, and analyzing the data with traditional nonlinear methods.

Hively et al., U.S. Pat. No. 5,815,413 discloses the applicability of nonlinear techniques to monitor machine conditions, such as the condition of a drill bit or the performance of an electrical motor driving a pump.

Clapp et al., U.S. Pat. No. 5,626,145 discloses the removal of artifacts representing eye blinks from EEG data using a zero-phase quadratic filter. As one normally skilled in the art can appreciate, the same method can remove other artifacts from data, such as quasi-periodic variations from three-phase electrical current, voltage, or power; and quasi-periodic oscillations from one or more channels of acceleration; and breathing artifacts from heart waves and chest sounds;.

Hively et al., U.S. Pat. No. 6,484,132 discloses a plurality of nonlinear techniques for using and enhancing phase space dissimilarity measures (PSDM) to forewarn of machine failures, as well as impending epileptic events from scalp EEG in ambulatory settings. PSDM yield superior performance over traditional nonlinear indicators, such as Kolmogorov entropy, Lyapunov exponents, and correlation dimension.

SUMMARY OF THE INVENTION

The present invention improves on prior disclosed methods involving the use of phase space dissimilarity measures (PSDM) to provide forewarning indications of critical events. Such events include failures in critical mechanical or electrical equipment, in medical treatment of human patients, and in many other applications.

The invention provides for better selection of process-indicative data for such analysis, such that one data channel can be used in place of multiple data channels without sacrificing consistent forewarning of critical events. Examples of such a process-indicative data are vibration power for mechanical systems, electrical power for electrically-driven machines, and differences between adjacent scalp EEG (electroencephalogram) channels.

The invention also provides a novel method to check the quality of the data, such that batches of inadequate quality data can be identified and replaced by adequate quality data.

The invention also provides a novel method including at least two separate filtering operations to remove both high-frequency and low-frequency artifacts using a zero-phase quadratic filter, which previously has been used only removing low-frequency artifacts in the prior art.

The invention also gives a novel method to combine several channels of time-serial data into a dC-dimensional multi-channel phase-space (PS) vector, which has the form: $\underline{s}_i = [s(1)_i, s(1)_{i+\lambda}, \ldots, s(1)_{i+(d-1)\lambda}, \ldots, s(C)_i, s(C)_{i\lambda}, \ldots s(C)_{i+(d-1)\lambda}]$. Here, $s_i(j)$ denotes the symbolized data for j-th channel at time $t_i$. C denotes the total number of data channels in the multi-channel phase-space reconstruction.

The invention also provides an end-of-life forewarning indicator (G), which is computed from a composite measure of dissimilarity ($C_i$). Here $C_i$ is the sum of the four renormalized PSDMs for the i-th subset:

$$C_i = U(X^2) + U(X_c^2) + U(L) + U(L_c) \tag{1}$$

The end-of-life indication (G) is quantified from this composite measure as follows. The appropriate process-indicative data is selected and acquired (for example) over 10-second snapshots at periodic intervals (such as once per minute), and then divided into subsets of N data points, which typically has a value in the range, $10{,}000 \leq N \leq 100{,}000$. The analysis then proceeds as follows: (a) each subset is artifact filtered; (b) the data in each subset is symbolized; (c) each subset is converted into a sequence of multi-channel phase-space vectors; (d) the phase-space vectors are tabulated into non-connected and connected phase-space distribution functions; (e) the distribution functions for each sequential test state (subset) are compared to the nominal state distribution functions via the four measures of dissimilarity in Eqs. (7)–(10); (f) each measure of dissimilarity is renormalized; (g) these four renormalized measures of dissimilarity are used to construct sequential values for the composite measure of condition change $C_i$ via Eq. (1); and (h) a standard least-squares method is used to fit several sequential values of $C_i$ to a straight line:

$$y_i = ai + b \tag{2}$$

We choose a window for this straight-line fit with a length of m=10 values of $C_i$ (and $y_i$ below), that is consistent with the number of data subsets in each data snapshot. Other values of m give inferior indication of condition change. Next, the variance, $\sigma_1^2$, measures the variability of the $C_i$ values about this straight-line fit:

$$\sigma_1^2 = \Sigma_i (y_i - C_i)^2 / (m-1) \tag{3}$$

Finally, the end-of-life statistical indicator, G, measures the variability of next m values of $C_i$ about an extrapolation of the straight-line fit as follows:

$$G = \Sigma_i (y_i - C_i)^2 / \sigma_1^2 \tag{4}$$

The index, i, runs over the m values of $C_i$ and $y_i$ in Eqs. (2)–(4). G has the form of a conventional chi-squared statistic, but that notation is not used to avoid confusion with the two chi-squared PSDMs, $U(X^2)$ and $U(X_c^2)$. Moreover, this disclosure does not use the G measure for a statistical test of null hypothesis. Rather in this invention, G is a relative measure, providing end-of-life forewarning, plus an indication of the failure onset.

Other objects and advantages of the invention, besides those discussed above, will be apparent to those of ordinary skill in the art from the description of the preferred embodiments, which follows. In the description reference is made to the accompanying drawings, which form a part hereof, and which illustrate examples of the invention. These examples, however are not exhaustive for the various embodiments of the invention, and therefore reference is made to the claims, which follow the description for determining the scope of the invention.

DETAILED DESCRIPTION OF THE PREFERRED EMBODIMENTS

The following description incorporates the methods disclosed in U.S. patent application Ser. No. 10/195,626 filed Jul. 12, 2002. To the extent that the methods of the present invention build upon the methods disclosed there, the disclosure of that application is hereby incorporated by reference.

The methods of this disclosure can be applied to electric motor predictive maintenance, other machinery and physical processes, as well as biomedical data for diagnosis and treatment of human patients. In one example, data sets were recorded in snapshots of 1.5 seconds, sampled at 40 kHz (60,000 total time-serial samples), including three-phase voltages and currents from an electric motor. The subsequent description describes analysis of an induced fault, referred to as a seeded fault.

Figure 1A:
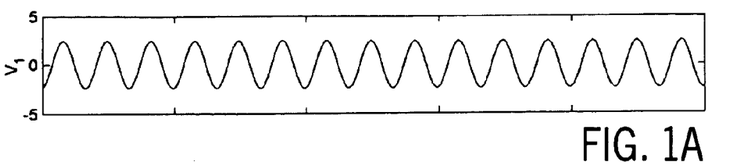
FIGS. 1A–1G show graphs of individual three-phase currents $I_i$, individual three-phase voltages $V_i$, and three-phase electrical power vs. time for an electric motor.
Figure 1B:
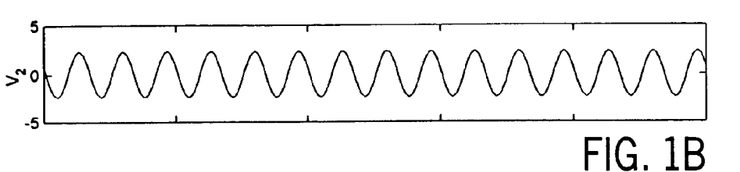
Figure 1C:
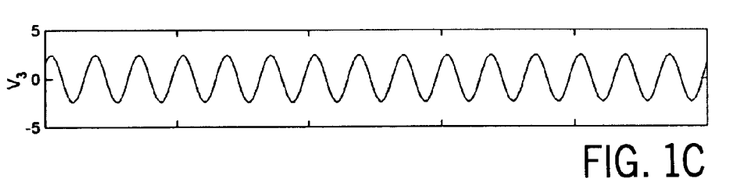
Figure 1D:
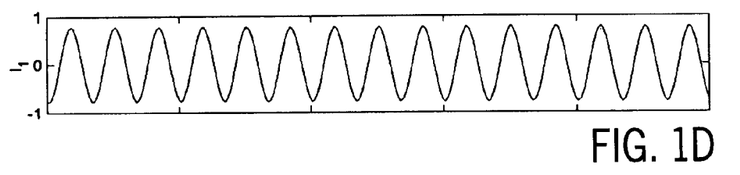
Figure 1E:
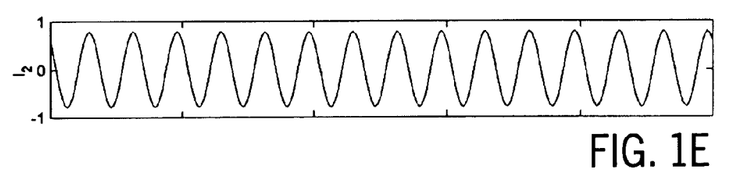
Figure 1F:
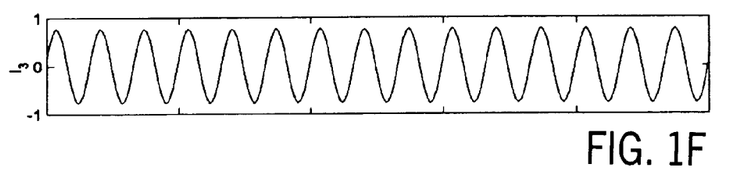
Figure 1G:
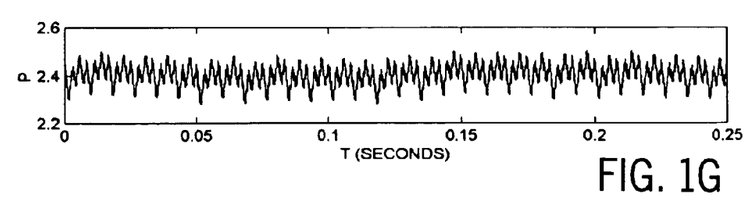
Figure 2A:
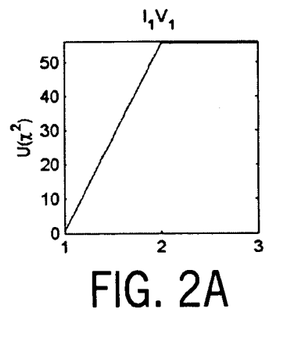
FIGS. 2A–2L show graphs of four phase-space dissimilarity measures (rows of subplots) vs. dataset number for the three components of three-phase electrical power data $I_iV_i$ from an air-gap seeded-fault in an electrical motor (columns of subplots)
Figure 2B:
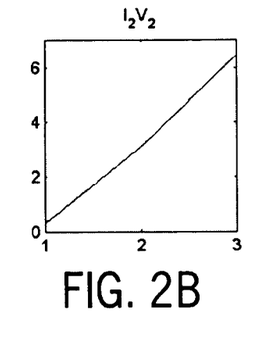
Figure 2C:
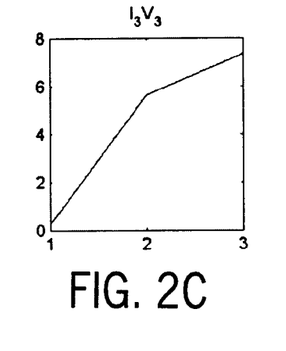
Figure 2D:
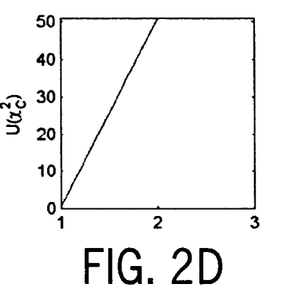
Figure 2E:
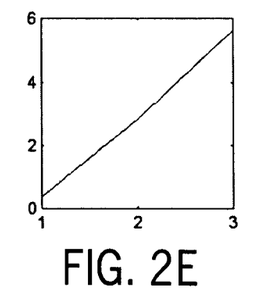
Figure 2F:
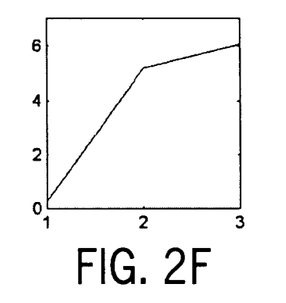
Figure 2G:
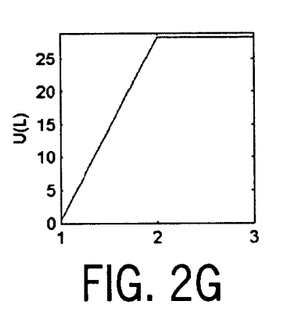
Figure 2H:
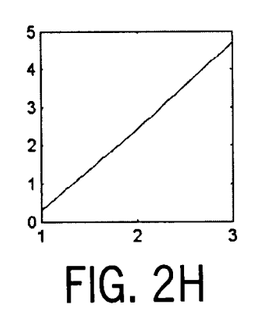
Figure 2I:
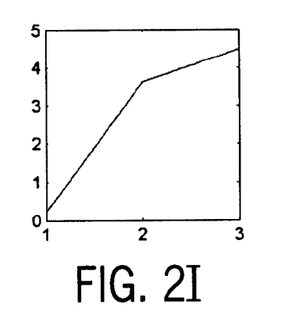
Figure 2J:
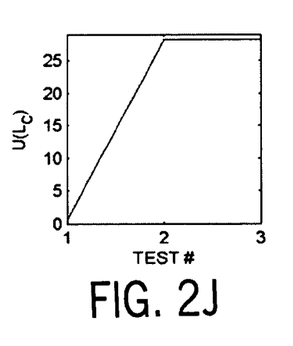
Figure 2K:
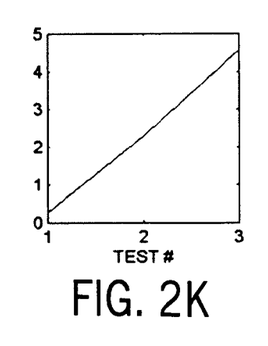
Figure 2L:
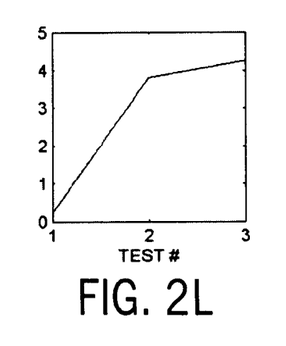

In such a motor, the components of the three-phase voltages ($V_i$) and currents ($I_i$), (see FIGS. 1A–1F) can be converted into an instantaneous motor power, $P=\Sigma_i I_i V_i$, where the sum runs over the three phases. The electrical power, P, (FIG. 1G) is advantageous in forewarning of critical events, because it reduces the number of data channels that must be analyzed to detect the condition change. The PSDM were computed for each of the three-phase currents and voltages separately, and compared with the condition change for components of the three-phase power. FIGS. 2A–2L show examples of the four dissimilarity measures for each component ($I_iV_i$) of three-phase power. All four dissimilarity measures of $I_2V_2$ (middle column) show an almost linear increase, and all four dissimilarity measures of $I_3V_3$ increase monotonically. All four dissimilarity measures of $I_1V_1$ increase from test #1 (no fault) to test #2 (first seeded fault), then remain constant from test #2 (first seeded fault) to test #3 (second seeded fault in addition to the first seeded fault). Thus, it was determined that the phase space dissimilarity measures (PSDM) method described above can extract condition change from one (or more) components of three-phase electrical power as well as from individual phase currents and voltages. The advantage of selecting electrical power as the process-indicative signal is the reduction in the number of channels of data for analysis.

The data for this same test also included tri-axial acceleration data from inboard (IB) and outboard (OB) motor locations. Vibration (mechanical) power can be determined from tri-axial acceleration, as follows. Acceleration, $\underline{a}$, is a three-dimensional vector that can be integrated once in time to give velocity (vector), $\underline{v} = \int \underline{a} dt$. Mass, m, times acceleration (vector) is force (vector), $\underline{F} = m\underline{a}$. The dot-product of force and velocity converts these vector quantities into the mechanical power (scalar), $P = \underline{F} \cdot \underline{v} = m\underline{a} \cdot \int \underline{a} \, dt$.

Figure 3A:
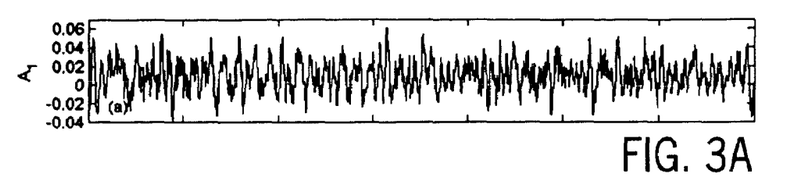
FIGS. 3A–3G show graphs of the three components of inboard acceleration $A_i$, the three components of inboard velocity $V_i$, and the resultant vibration (mechanical) power.
Figure 3B:
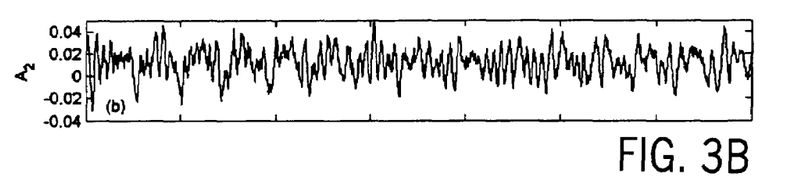
Figure 3C:
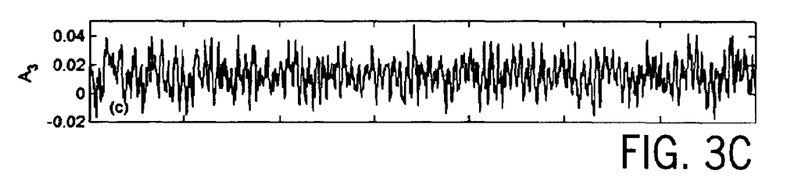
Figure 3D:
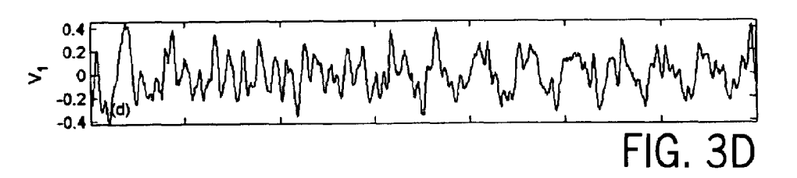
Figure 3E:
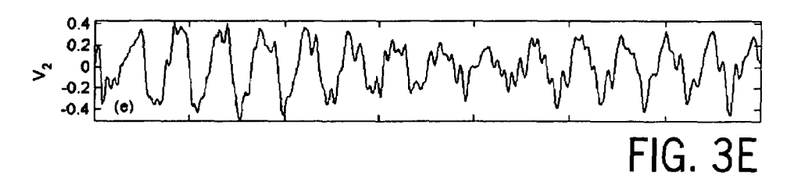
Figure 3F:
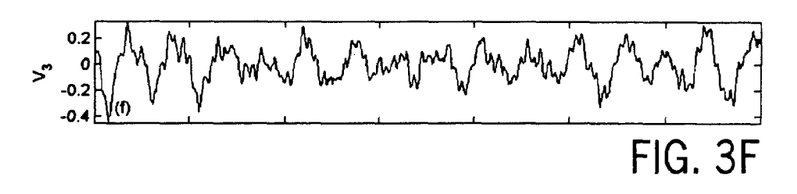
Figure 3G:
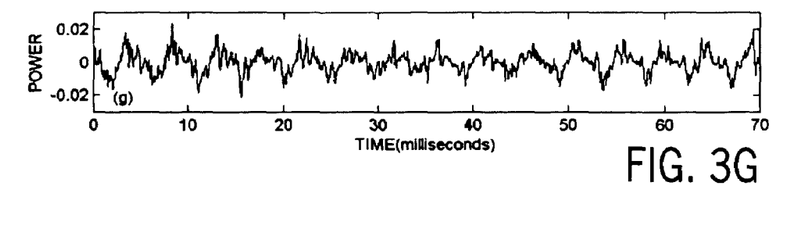
Figure 4A:
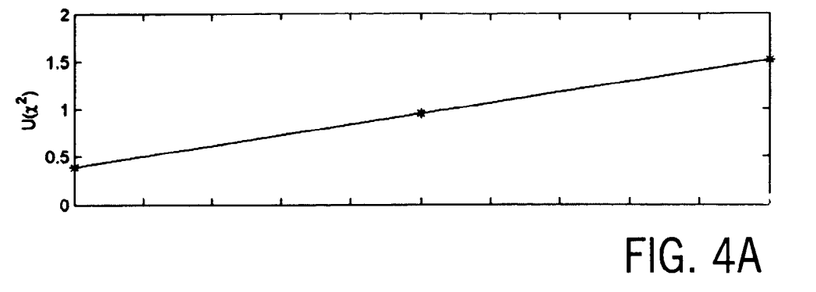
FIGS. 4A–4D are graphs of four dissimilarity measures vs. the dataset number from the air-gap seeded-fault vibration power.
Figure 4B:
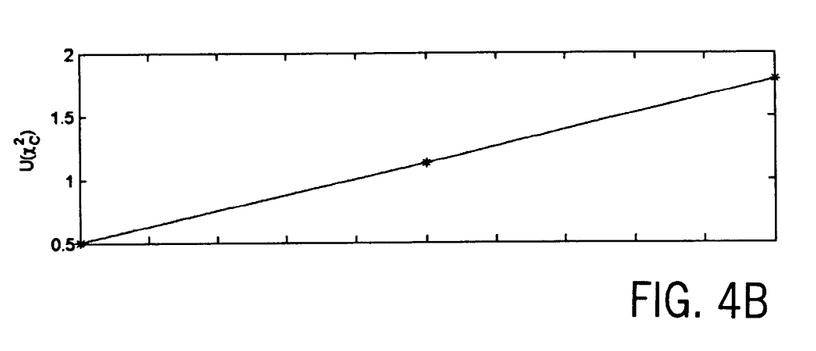
Figure 4C:
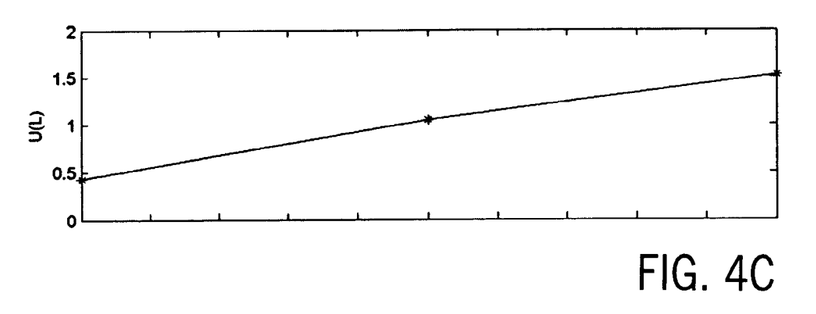
Figure 4D:
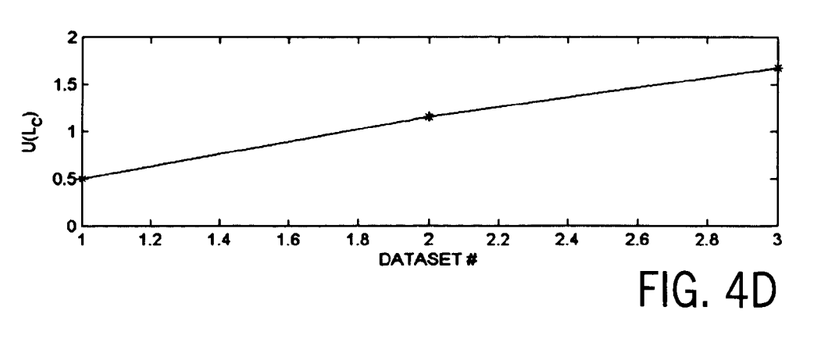

FIGS. 3A–3G show the three components of inboard acceleration (FIGS. 3A–3C), as well as the corresponding three components of inboard velocity (FIGS. 3D–3F). The noteworthy feature of these plots is the clear periodicity with additional complex nonlinear features, which also appear in the resulting vibration power (FIG. 3G).

FIGS. 4A–4D show a nearly linear rise in all four PSDM as computed from the vibration power of the previous paragraph. To obtain this result, a sequence of single parameter searches was executed: varying S with $\lambda$ fixed, then varying λ with S set to the value from the first search. This approach, yielded S=85 and λ=42 for d=3. Other dimensions (d=2 and 4) give inferior results. Subsequently, an exhaustive search was made over a range of S and λ for d=3 to obtain best condition change at S=84 and λ=47.

The above examples show that electrical power has renormalized values of PSDM in the range of 5–55 standard deviations from the mean; two of the PSDM rise monotonically (not linearly), thus yielding less desirable change discrimination. It was found that vibration power has PSDM values on the order of unity; all four PSDM increase linearly, thus yielding good change discrimination. A search to find one (or more) data channels for consistent event forewarning requires the analysis of all three components of acceleration, or all three components of velocity, or all three components of three-phase electrical power, or all six components of three-phase voltage and current. However, only one channel of electrical power or one of vibration (mechanical) power needs to be analyzed to obtain consistent failure forewarning. As one normally skilled in the art can readily appreciate, the savings in computation effort is an important and novel improvement to the art.

Figure 5:
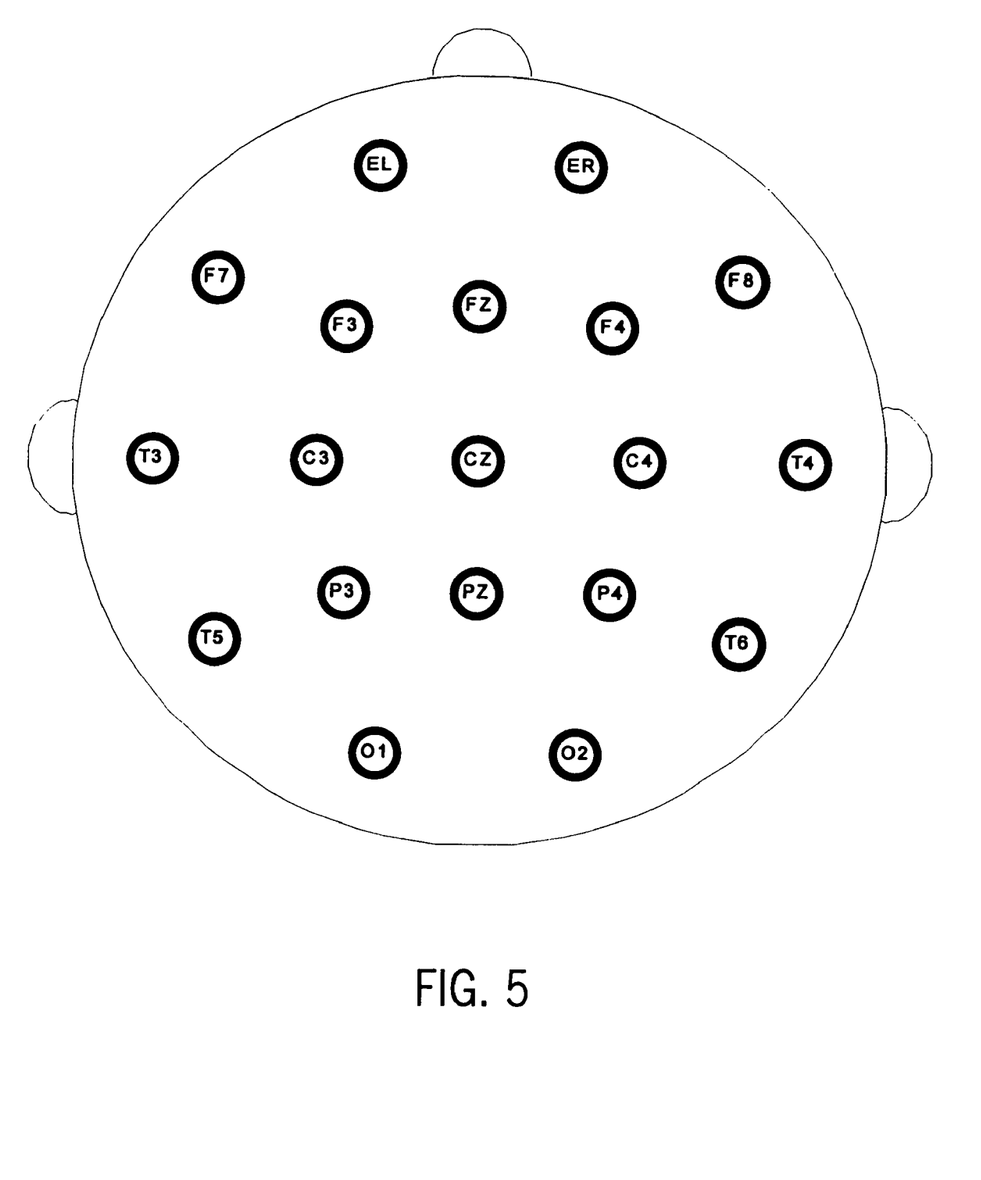
FIG. 5 shows the placement of monopolar scalp EEG electrodes on the head of a human patient (as viewed by looking down on the head from above, with the nose at the top, and ears on the left and right sides), each of which measures a local voltage with respect to some reference electrode.

Another example uses multi-channel EEG data that is combined into a multi-channel PS reconstruction for critical-event forewarning. FIG. 5 shows an array of monopolar scalp EEG electrodes, each of which measures a local voltage with respect to some reference electrode. The voltage difference between adjacent monopolar electrodes creates a "bipolar montage." One bipolar channel is (for example) the difference, F4–C4, on the right hemisphere; another is F3–C3 on the left hemisphere. Each bipolar channel extracts a time-serial signal that potentially allows removal of most locally-generated artifacts, while retaining a differential measure of the brain activity. Our analysis of EEG data has determined that data from the bipolar montage without artifact filtering provides a reasonable alternative to artifact filtering, yielding better forewarning than the monopolar montage with (or without) artifact filtering (and not much different from bipolar forewarning with artifact filtering). Moreover, two (or more) of these bipolar channels can be combined via the multi-channel phase-space vector, to provide forewarning of epileptic seizures that is comparable to the analysis of all nineteen of the individual monopolar channels. As one normally skilled in the art can readily appreciate, the savings in computational effort (one two-channel bipolar PS reconstruction vs. nineteen individual PS reconstructions) is an important and novel improvement.

After choosing the appropriate process-indicative data in a manner that reduces the analysis effort, as discussed above, the present invention next provides an improved method to identify inadequate quality data. Raw process-indicative data can come from a variety of sensors, such as electroencephalogram data, electrocardiogram data, chest sounds, single- or multi-axial accelerometer(s), single- or multi-phase motor current(s) and voltage(s). This data is sampled at equal time intervals, τ, starting at time $t_0$, yielding a sequence of time serial data, $x_i = x(t_0 + i\tau)$, i=1, 2, . . . , N. These signals are digitized and recorded as either integer or decimal numbers, which have a range between from some minimum value ($x_{min}$) to maximum value ($x_{max}$).

Figure 6A:
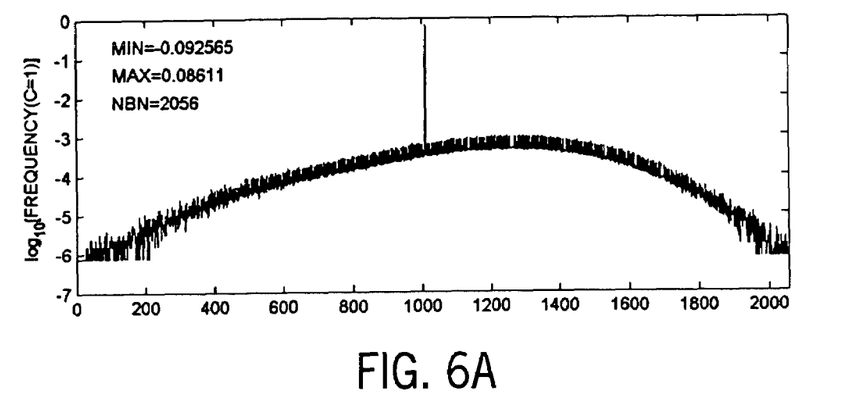
FIGS. 6A–6C are graphs of three channels of acceleration data vs. BIN number for a machine test.
Figure 6B:
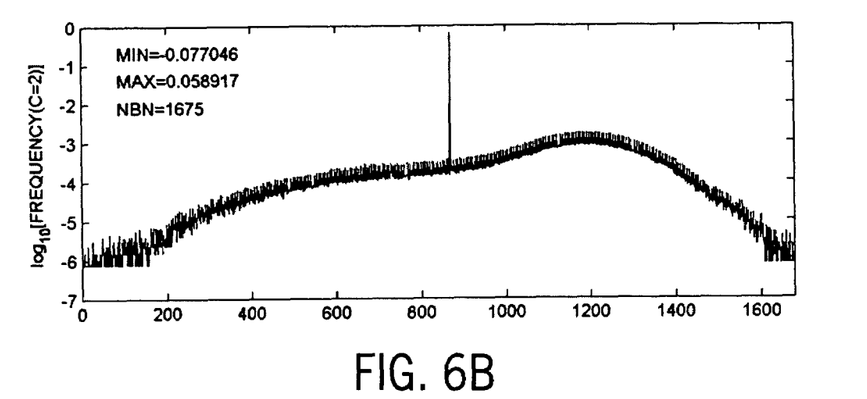
Figure 6C:
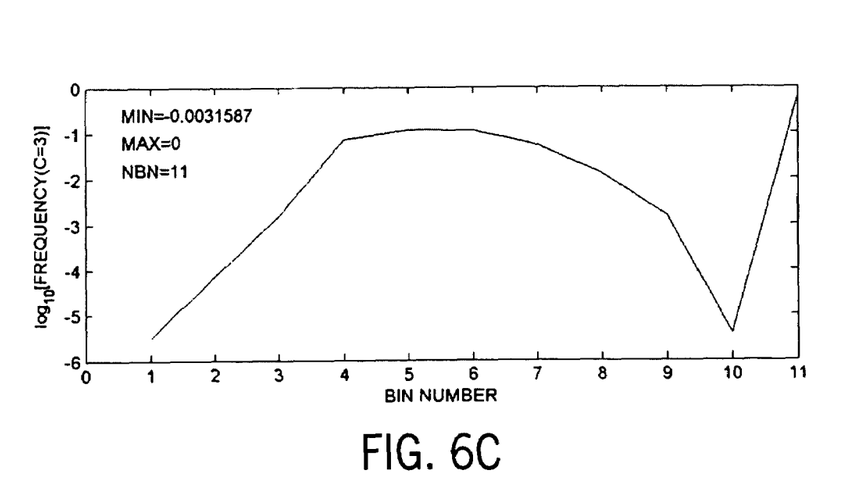
Figure 7A:
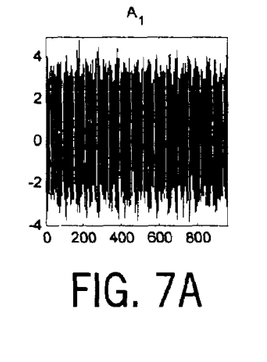
FIGS. 7A–7L show samples of the three components $A_i$ of tri-axial acceleration data for the air-gap seeded-fault test over successively shorter time intervals, displaying complex, nonlinear features.
Figure 7B:
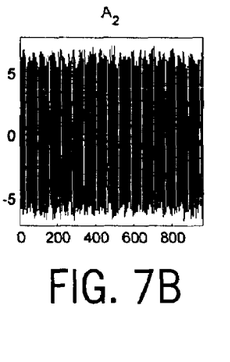
Figure 7C:
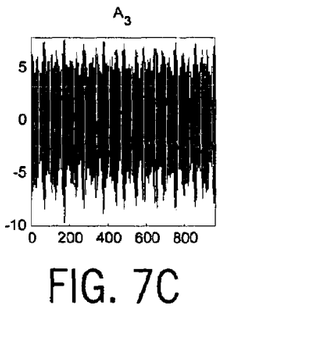
Figure 7D:
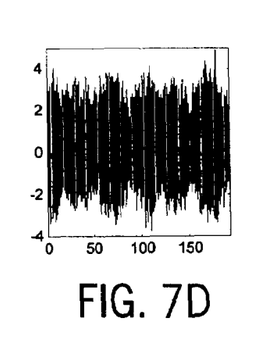
Figure 7E:
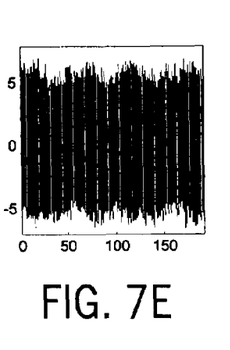
Figure 7F:
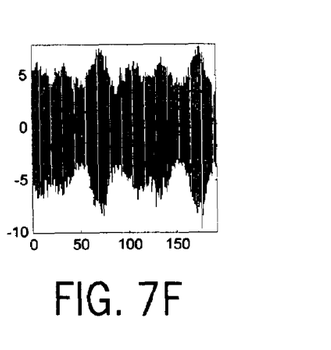
Figure 7G:
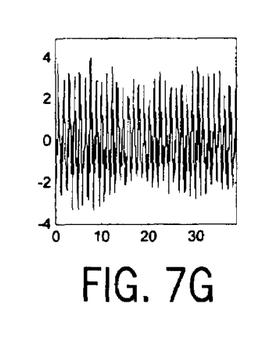
Figure 7H:
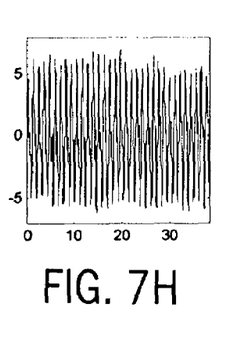
Figure 7I:
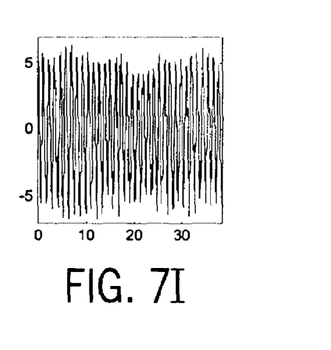
Figure 7J:
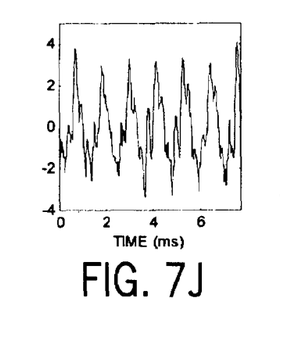
Figure 7K:
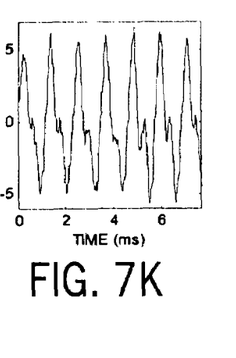
Figure 7L:
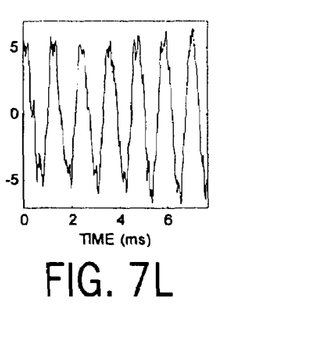
Figure 8A:
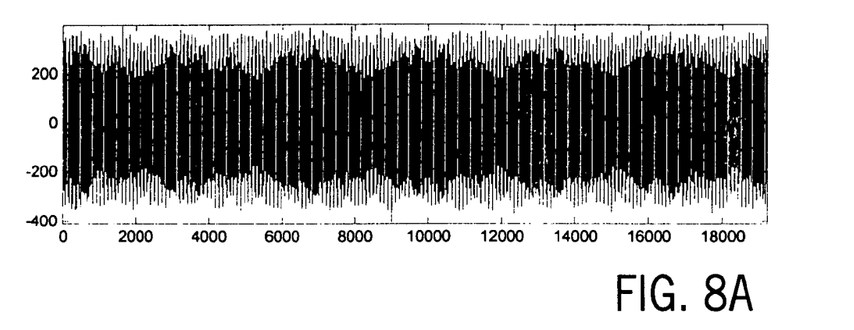
FIGS. 8A–8D are graphs of vibration power over successively shorter time intervals, showing complex, nonlinear features.
Figure 8B:
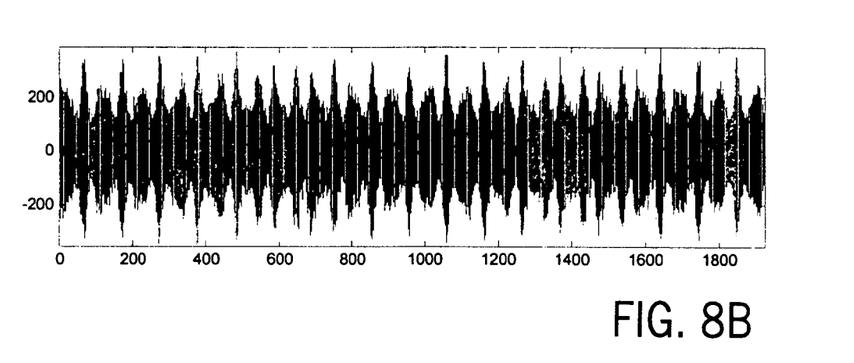
Figure 8C:
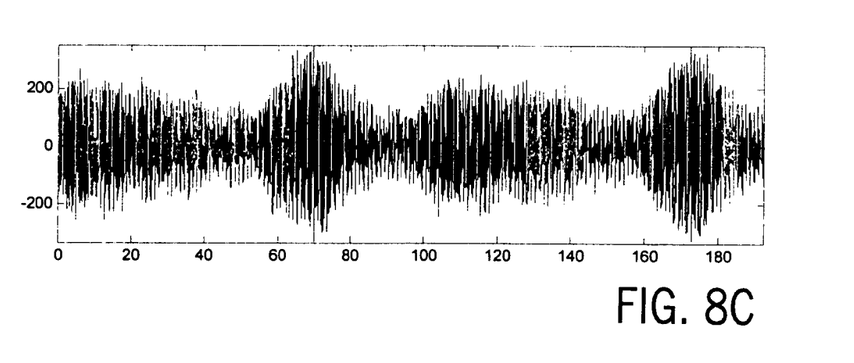
Figure 8D:
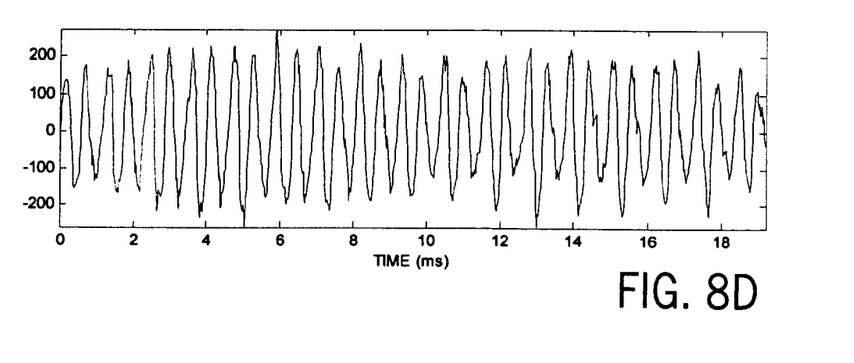

Determination of the data quality from the time serial data, $x_i$, involves the following steps: (a) sorting the $x_i$ values into ascending order from $x_{min}$ to $x_{max}$; (b) determining the number of unique signal values (n); (c) obtaining the occurrence frequency ($F_k$) for each unique signal value ($v_k$); (d) estimating the occurrence probability for a single outlier in a normal distribution by solving: $1/n = \frac{1}{2} \text{erfc}(z/\sqrt{2})$. Here, n is the number of unique signal values from step (b); erfc is the complementary error function; z is the number of standard deviations from the mean for such a single outlier; and the mean occurrence frequency is estimated as N/n. Next, (e) plotting $F_k$ versus $v_k$ in each BIN, as shown (for example) in FIGS. 6A–6C; (f) reject any outlier bin with $[v_k - (N/n)]/\sigma_3 > z$, where $\sigma_3$ is the standard deviation of the occurrence frequency over all of the unique signal values from step (b). In this example, FIGS. 6A–6C show frequency distributions from real test data. Huge spikes in $\log_{10}$FREQUENCY occur above the underlying baseline (top two subplots for channel 1 (C1) and channel 2 (C2), indicating an accumulation of data values in one (or a few) unique signal value(s). These spikes far exceed the above limit. Another problem is that the c1- and c2-signals have a narrow range of values (–0.099 to +0.089), indicating that the signal is improperly scaled for digitization. Moreover, the c1- and c2-distribution functions have large variability, which further indicates excessive noise.

Table 1 summarizes the results for samples of tri-axial accelerometer data that was acquired from a test motor. The data were sampled for 10 seconds at 128 kHz for a total of 1,280,000 points from a shaft crack test. The table below shows the minimum (min) and maximum (max) values by dataset for each of three accelerometer channels (c1–c3).

TABLE 1

| Tri-axial Acceleration Data | | | | | | | |
|---|---|---|---|---|---|---|---|
| DATASET | min (c1) | max (c1) | min (c2) | max (c2) | min (c3) | max (c3) | #BINS (c3) |
| FSF40c3 | –.08755 | +.07760 | –.08748 | +.06009 | –.00323 | –.00254 | 11 |
| FSF20c5 | –.08899 | +.07375 | –.08247 | +.05514 | –.00322 | –.00261 | 10 |
| FSF20c4 | –.09895 | +.07684 | –.08893 | +.05906 | –.00316 | –.00261 | 9 |
| UNCRc1 | –.09257 | +.08611 | –.07705 | +.05892 | –.00316 | 0.0 | 11 |
| UNCRc3 | –.08549 | +.07725 | –.08364 | +.05572 | –.00309 | –.00247 | 10 |

These data have discrete values with five significant figures (x.xxxx) for all three channels. The right-most column of Table 1 (with the header "#BINS") shows the number of different discrete c3-values, which varies between nine and eleven over a very narrow range of signal values (–0.0032 to +0.0026). This small number of discrete signal values is also seen in FIG. 6C, corresponding to a data precision of $\log_2(11) = 3.45$. This low data precision is well below that attainable by modern data acquisition systems, which can acquire data with >10 bits of precision, and more typically 16 (or more) bits. Thus, the c3-signal is due to bit chatter (noise), rather than a real signal.

Rejection of this inadequate quality data from further analysis avoids meaningless or nonsensical results. In the prior art represented by U.S. Pat. No. 5,815,413, the data range was partitioned into an equal number of non-overlapping uniform-size bins to obtain the occurrence frequency. The improvement of this disclosure is the use of the unique signal values in the raw data. As one of ordinary skill in the art can appreciate, this novel improvement uses the explicit features in the data to determine its quality, rather than artificial constructs of the prior art (such as analyst-chosen bins to tabulate the occurrence distribution function).

Data of the types discussed above, may also have artifacts that would otherwise confound the analysis, and therefore must be removed. In Clapp et al., U.S. Pat. No. 5,626,145, "Method and Apparatus for Extraction of Low-Frequency Artifacts from Brain Waves for Alertness Detection," a method to remove low-frequency artifacts (such as eye-blinks in EEG data or breathing artifacts from ECG data) via a zero-phase quadratic filter is disclosed. This filter uses a moving window of process-indicative data points, $e_i$, with the same number of data points, w, on either side of a central point. A quadratic curve is fitted in a least-squares sense to these 2w+1 data points. The central point of this fit is taken as the best estimate of the low-frequency artifact, $f_i$. The residual signal, $g_i=e_i-f_i$, has essentially no low-frequency artifact activity.

However, data may have both low-frequency artifacts (such as eye-blinks in EEG, or breathing in electrocardiogram, ECG, data), and high-frequency artifacts (such as 60-Hz noise in ECG). The novel improvement taught in this disclosure is application of the original zero-phase quadratic filter first to extract the low-frequency $f_i$-data of the previous paragraph using an appropriate (small) value for the filtering-window width, w, which effectively removes the high-frequency artifacts. Subsequently, the same filter is applied to this $f_i$-data with an appropriate (large) filtering window width for w, which removes the low-frequency artifacts from the resultant second-stage $g_i$-data of the previous paragraph. The use of the zero-phase quadratic filter in two stages as applied to PSDM data analysis has not been seen in the prior art and improves forewarning analysis, for example in ECG data with both low-frequency breathing artifacts and high-frequency 60-Hz noise. As one normally skilled in the art can appreciate, the removal of both low- and high-frequency artifacts while preserving the nonlinear data features is an important and novel component of the analysis.

Next, each artifact-filtered value, $g_i$, is converted into a symbolized form, $s_i$, that is, one of S different integers, 0, 1, ..., s−1:

$$0 \le s_i = \text{INT}[S(g_i - g_{min})/(g_{max} - g_{min})] \le S-1 \quad (5)$$

Here, the function INT converts a decimal number to the closest lower integer; $g_{min}$ and $g_{max}$ denote the minimum and maximum values of artifact-filtered data, $g_i$, respectively, over the baseline (nominal state) data. To maintain S distinct symbols, the following expression holds, namely $s_i=S-1$ when $g_i=g_{max}$. Expression (5) creates symbols that are uniformly spaced between the minimum and maximum in signal amplitude (uniform symbols). Alternatively, one can use equiprobable symbols, by ordering all N base case data points from the smallest to the largest value. The first N/S of these ordered data values correspond to the first symbol, 0. Ordered data values (N/S)+1 through 2N/S correspond to the second symbol, 1, and so on up to the last symbol, S−1. By definition, equiprobable symbols have non-uniform partitions in signal amplitude and present the advantage that dynamical structure arises only from the phase-space reconstruction. Large negative or positive values of $g_i$ have little effect on equiprobable symbolization, but significantly change the partitions for uniform symbols. Moreover, the mutual information function is a smooth function of the reconstruction parameters for equiprobable symbols, but is a noisy function of these same parameters for uniform symbols. Thus, equiprobable symbols provide better indication of condition change than uniform symbols when constructing a (non)connected phase space.

Phase-space (PS) construction uses time-delay vectors, $\underline{s}_i = [s_i, s_{i+\lambda}, \ldots, s_{i+(d-1)\lambda}]$ to unfold the underlying dynamics. Critical parameters in this approach are the time delay, $\lambda$, and system dimensionality, d, and the type and number of symbols, S. However, information exchange between (for example) complex machinery components or between different brain locations connect the local processes. This disclosure provides a novel method to combine several channels of time-serial data into a multi-channel phase-space (PS) reconstruction, which has the form of a dC-dimensional vector: $\underline{s}_i = [s(1)_i, s(1)_{i+\lambda}, \ldots, s(1)_{i+(d-1)\lambda}, \ldots, s(C)_i, s(C)_{i+\lambda}, \ldots s(C)_{i+(d-1)\lambda}]$. Here, $s_i(j)$ denotes the symbolized data for j-th channel at time $t_i$. C denotes the total number of data channels in the multi-channel phase-space reconstruction.

Conversion of the multi-channel time serial data to a sequence of phase-space vectors via the method of the previous paragraph divides the phase space into $S^{Cd}$ discrete bins, which are uniquely labeled via base-S arithmetic:

$$0 \le y(i) = y(\underline{s}_i) = \sum_{j=1}^{c} \sum_{k=1}^{d-1} s(j)_{i+k\lambda} S^{k+d(j-1)} \le S^{Cd} - 1 \quad (6)$$

The resulting distribution function (DF) is a discretized density, which is obtained by counting the number of points that occur in each phase space bin. The population of the ith bin of the distribution function, is denoted $Q_i$, for the base case, and $R_i$ for a test case, respectively.

The test case is compared to the base case via dissimilarity measures between $Q_i$ with $R_i$ that are defined by:

$$\chi^2 = \sum_i (Q_i - R_i)^2 / (Q_i + R_i), \quad (7)$$

$$L = \sum_i |Q_i - R_i|, \quad (8)$$

Here, the summations run over all of the populated phase space cells. These measures account for changes in the geometry and visitation frequency of the resultant geometric object, called an "attractor." The $X^2$ measure is one of the most powerful, robust, and widely used statistics for comparison between observed and expected frequencies. In this context, $X^2$ is a relative measure of dissimilarity, rather than an unbiased statistic for accepting or rejecting a null statistical hypothesis. The L distance is the natural metric for distribution functions by its direct relation to the total invariant measure on the phase-space attractor. Consistent calculation of these measures obviously requires the same number of points in both the base case and the test case distribution functions, identically sampled; otherwise, the distribution functions must be properly rescaled.

The process dynamics yield successive PS points, as prescribed by $\underline{s}_i \to \underline{s}_{i+1}$. Thus, a discrete representation of the process flow is obtained in the form of a 2dC-dimensional multi-channel PS vector, $\underline{S}_i=[\underline{s}_i, \underline{s}_{i+1}]$, that is formed by adjoining two successive vectors from the dC-dimensional reconstructed PS. $S_i$ is a vector for the multi-channel connected phase space (CPS). As before, Q and R denote the CPS distribution functions for the base case and test case, respectively. The measure of dissimilarity between the two distribution functions for the CPS, signified by the "c" subscript are thus defined as follows:

$$\chi_c^2 = \sum_{ij} (Q_{ij} - R_{ij})^2 / (Q_{ij} + R_{ij}) \tag{9}$$

$$L_c = \sum_{ij} |Q_{ij} - R_{ij}|. \tag{10}$$

The first subscript in Eqs. (9)–(10) denotes the initial PS point, and the second subscript denotes the sequel PS point in the CPS pair. These CPS measures have higher discriminating power than unconnected PS measures of dissimilarity. Indeed the measures defined in Eqs. (7)–(10) satisfy the following inequalities: $X^2 \leq L$, $X_c^2 \leq L_c$, $L \leq L_c$, and $X^2 \leq X_c^2$, where $X_c^2$ and $L_c$ are dissimilarity measures for connected phase space and $X^2$ and L are dissimilarity measures for non-connected PS.

To assure robustness, the construction of the base case data requires careful statistics to eliminate outlier base case subsets. For a description of this part of the methodology, reference is made to Hively, U.S. patent application Ser. No. 10/195,626 filed Jul. 12, 2002.

A consistent method of comparison is needed to interpret the disparate range and variability of the dissimilarity measures. To this end, the dissimilarity measures are renormalized, as described next. The B non-outlier base case subsets from the previous paragraph are compared to each test case subset, to obtain the corresponding average dissimilarity value, $V_i$, of the ith subset for each dissimilarity measure. Here, V denotes each dissimilarity measure from the set, $V=\{L, L_c, X^2, \text{ and } X_c^2\}$. The mean value, $\underline{V}$, and the corresponding standard deviation, $\sigma_2$, of the dissimilarity measure V are calculated by comparison of all of the unique pairs of base case subsets, after the outliers have been eliminated. The renormalized dissimilarity is the number of standard deviations that the test case deviates from the base case mean: $U(V)=|V_i-\underline{V}|/\sigma_2$.

Once the renormalized measures for the test and base cases have been obtained, a threshold, $U_c$, is selected for each renormalized measure U to distinguish between normal (base) and possibly abnormal (test) regimes. The choice of a reasonable threshold is critical for obtaining robust, accurate, and timely results. A forewarning indication is obtained when a renormalized measure of dissimilarity exceeds the threshold, $U \geq U_c$, for a specified number, $N_{OCC}$, of sequential occurrences.

The remainder of the PSDM analysis is described by Hively, U.S. patent application Ser. No. 10/195,626 filed Jul. 12, 2002, cited above. As one normally skilled in the art can readily appreciate, the novel improvement to the prior art involves combining multiple-channel time-serial data into a one multi-channel time-delay phase-space (PS) reconstruction, rather than performing the PS reconstruction for each of several channels.

Figure 9A:
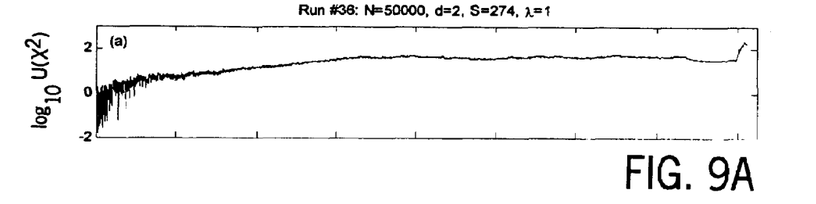
FIGS. 9A–9F show graphs of phase-space dissimilarity measures from vibration power versus time: (a)–(d) the four renormalized PSDM; (e) composite measure, $C_i$, of the four PSDM; (f) end-of-life indicator, G (solid), running maximum of G (dashed), and ratio, R, of successive maxima (-.-) in G.
Figure 9B:
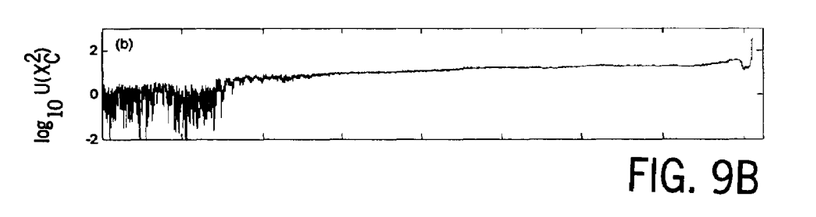
Figure 9C:
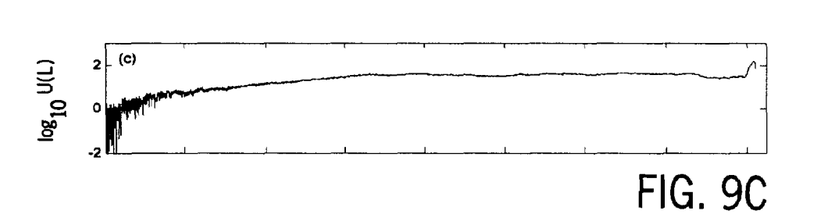
Figure 9D:
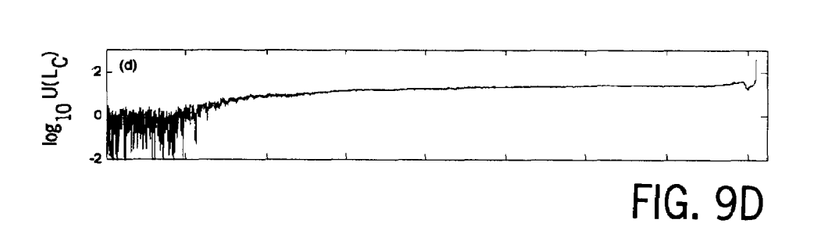
Figure 9E:
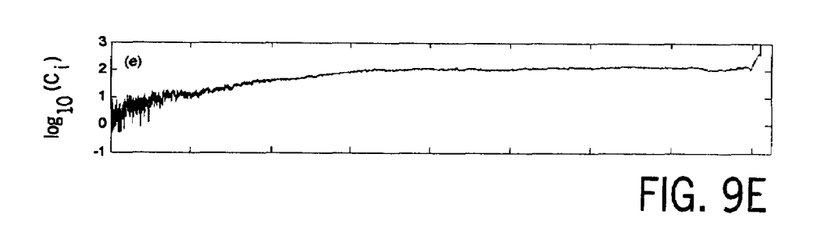

An alternative embodiment of this invention is illustrated by the following example. The vibration power data, as discussed above, was acquired in 10-second snapshots at 50 kHz at fifteen-minute intervals; see Table 2 for the interval ($\Delta\tau$) between each snapshot. Each 500,000-point snapshot was divided into ten non-overlapping subsets of 50,000-points each for subsequent analysis. This data characterized an accelerated-failure test of an over-loaded gearbox. The test protocol involves a break-in period at the nominal (1×) load (530 ft-lbs) for one hour, followed by twice (2×) or three times (3×) the normal load, as shown in Table 2 The end-of-life failure included pinion gear damage, broken teeth, and a sheared shaft. The failure occurred after 162.5 hours, corresponding to 650 snapshots. FIGS. 7A–7L show the very complex, nonlinear features in the three components of the tri-axial accelerometer data ($\underline{a}$). The individual snapshots were combined into one long dataset (12.7 GB). Acceleration was subsequently converted to a long stream (4.1 GB) of vibration power (FIGS. 8A–8D), using the previously described method to convert tri-axial acceleration into power via time-integration to velocity ($\underline{v}=\int \underline{a} dt$) with a subsequent vector dot-product to produce power (P~$\underline{a}\cdot\underline{v}$). FIGS. 9A–9D show the PSDM from this data. The phase-space parameters are N=50,000, S=274, d=2, λ=1. All four dissimilarity measures rise systematically (FIGS. 9A–9D) to provide forewarning of the failure. However, a more robust and specific end-of-life (EOL) indicator is needed. We observe that all four of the PSDMs have similar tends, suggesting the definition of a composite measure, $C_i$, as the sum of the four renormalized PSDMs for the i-th dataset (FIG. 9E):

$$C_i = U(X^2) + U(X_c^2) + U(L) + U(L_c) \tag{11}$$

This composite measure is expected to be more robust than any one of the individual measures of phase space dissimilarity, while accurately indicating condition change. Subsequent description presents another novel improvement of this disclosure to provide end-of-life forewarning, and indication of failure onset.

The end-of-life indication from the composite measure of the previous paragraph is quantified as follows. We use contiguous, non-overlapping windows of $C_i$ to obtain the best straight-line fit in a least-squares sense:

$$y_i = ai + b \tag{12}$$

The window length of m=10 values of $C_i$ (and $y_i$ below) is chosen consistent with the number of subsets in each snapshot. Other values of m give inferior indication of condition change. Next, the variance, $\sigma_1^2$, measures the variability of the $C_i$ values about this straight-line fit:

$$\sigma_1^2 = \Sigma_i (y_i - C_i)^2 / (m-1) \tag{13}$$

Other fits (such as, quadratic, cubic, and quartic) give inferior condition change indication, due to the poor extrapolation outside the fitting window. Finally, G measures the variability of next m values of $C_i$ about an extrapolation of this straight-line:

$$G = \Sigma_i (y_i - C_i)^2 / \sigma_1^2 \tag{14}$$

Figure 9F:
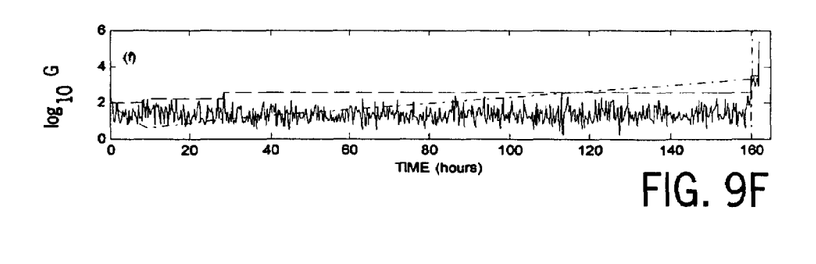

The index, i, in Eqs. (12)–(14) runs over the m values of $C_i$ and $y_i$. Note that G has the form of a conventional chi-squared statistic, but we do not use that notation to avoid confusion with the two $X^2$ PSDMs, $U(X^2)$ and $U(X_c^2)$. A statistical test for G would involve (for example) the null hypothesis that deviations from the straight-line fit are normally distributed. Standard chi-squared statistical tables give the corresponding value of $G \leq 28.5$ for m=10 degrees of freedom with a probability of one out of the number (650) of snapshots (1/650~1.5×10$^{-3}$). However, we observe many instances with G>28.5 throughout this test sequence. These outliers occur because the underlying tri-axial acceleration has dynamical correlations, thus violating the requirement for independent, identically distributed samples. Instead, we use G (solid curve in FIG. 9F) as a relative measure of end-of-life. As time moves forward, we obtain the running maximum of G, as the larger of G and $G_{max}$ (dashed curve in FIG. 9F). We neglect the first six G-values (for example) to avoid startup transients. This running maximum rises in modest increments to 376 over the first 159.75 hours of the test, while intermediate values of G fall well below $G_{max}$. The chain curve (-.-) in FIG. 9F is the ratio, $R=(G_{max})_k/(G_{max})_{k-1}$, of the current running maximum in G, $(G_{max})_k$, to the previous maximum in G, $(G_{max})_{k-1}$. $G_{max}$ rises to 2,493 at 160 hours, with a corresponding R=6.62, which is well above the largest non-end-of-life value, R=2.22, at 2 hours. Thus, G provides clear end-of-life forewarning, plus indication of the failure (G=244,655). Table 2 gives: (a) the largest non-EOL value of R ($R_{NEOL}$) and the corresponding value of G ($G_{NEOL}$); (b) values of R ($R_{EOL}$) and G ($G_{EOL}$) that indicate the end of life, and the matching time ($T_{EOL}/T_{FAIL}$); (c) the value of G at failure onset ($G_{ONSET}$) and the corresponding time ($T_{ONSET}/T_{FAIL}$); and (d) the failure-endpoint time ($T_{FAIL}$).

TABLE 2

Summary of Gearbox Overload Results

| Run | Over-load | Δτ min. | $R_{NEOL}$ | $G_{NEOL}$ | $R_{EOL}$ | $G_{EOL}$ | $T_{EOL}/T_{FAIL}$ | $G_{ONSET}$ | $T_{ONSET}/T_{FAIL}$ | $T_{FAIL}$ hr. |
|---|---|---|---|---|---|---|---|---|---|---|
| 36 | 2X | 15 | 2.22 | 376 | 6.62 | 2,493 | .985 | 244,655 | 0.998 | 162.50 |
| 37 | 3X | 1 | 1.79 | 333 | 8.07 | 2,690 | .956 | 16,284 | 0.996 | 8.55 |
| 38 | 3X | 1 | 6.20 | 374 | 11.71 | 13,486 | .938 | 48,379 | 0.990 | 4.02 |
| 39 | 2X | 1 | 2.32 | 853 | 3.89 | 5,231 | .980 | 5,231 | 0.980 | 8.60 |
| 39 | 3X | 1 | 2.88 | 1,151 | 29.03 | 33,415 | .972 | 44,552 | 0.994 | 8.60 |

Runs #36–38 have largest non-EOL values: $R_{NEOL}$=6.20 and $G_{NEOL}$=376. The smallest EOL values are: $R_{EOL}$=6.62 and $G_{EOL}$=2,493. Thus, limits (for example) of R>6.4 and G>1,800 provide EOL forewarning. Moreover, we find that the largest EOL value of $G_{EOL}$=13,486, while the smallest failure-onset value is $G_{ONSET}$=16,284. Thus, an intermediate value (for example) of G>15,000 distinguishes the EOL from failure onset forewarning This approach gives quantitative limits for transitions from nominal operation (green-light in a traffic signal metaphor), to forewarning of failure (yellow light for caution), and finally to failure onset (red-light for stop).

Run #39 involves a different test protocol: a one-hour break-in period at nominal load (1×), followed by 2× load for two hours, after which the load alternates between 3× and 2× loads for ten and five minutes, respectively. Run #39 seeks failure forewarning in the presence of load changes. Table 2 shows that the above limits for G and R also distinguish between the non-EOL (green) and EOL (yellow) states for the 3×-portion of this test, because the higher overload drives the failure. These limits do not apply to the 2× test, due to the reduced damage at the lower overload. Unsurprisingly, a different limit of G>38,000 (for example) distinguishes between the EOL and failure onset forewarnings, due to the change in test protocol. The green-yellow-red traffic-signal metaphor still applies for this test.

As one of ordinary skill in the art can appreciate, these examples give quantitative limits for transitions from normal operation (normal condition), to forewarning of failure (caution condition), and finally to failure onset (critical event), as a novel improvement in the art.

This has been a description of detailed examples of the invention. These examples illustrate the technical improvements, as taught in the present invention. It will be apparent to those of ordinary skill in the art that certain modifications might be made without departing from the scope of the invention, which is defined by the following claims.

I claim:

1. A method for processing data to provide a forewarning of a critical event, comprising:

acquiring a plurality of sets of data for a plurality of channels of data from monitoring at least one physical test subject or physical process;

calculating a set of channel data for a selected parameter from the plurality of channels of data representing parameters that are calculated to provide the selected parameter;

computing a renormalized measure of dissimilarity from distribution functions derived from a phase space for a selected channel of data;

comparing said renormalized measure of dissimilarity to a threshold ($U_C$) for a number of occurrences ($N_{OCC}$) to indicate a condition change in said renormalized measure of dissimilarity; and detecting a simultaneous condition change in a plurality ($N_{SIM}$) of renormalized measures of dissimilarity to determine a forewarning of the critical event; and providing an output of at least one of a graph, a table of data or an observable signal by which a human observer can detect the forewarning of the critical event.

2. The method of claim 1, wherein the test subject is a human patient.

3. The method of claim 1, wherein the test subject is a mechanical device or physical process.

4. The method of claim 1, wherein the selected parameter is three-phase electrical power.

5. The method of claim 1, wherein the selected parameter is vibration mechanical power.

6. The method of claim 1, wherein the selected parameter is a difference between two channels of EEG data.

7. The method of claim 1, further comprising:

performing a first filtering of each set of data with a zero-phase quadratic filter that filters out high-frequency artifacts; and performing a second filtering of each set of data with a zero-phase quadratic filter to filter out low-frequency artifacts.

8. The method of claim 1, further comprising:
sorting data values into ascending order from a minimum to a maximum;
determining a number of unique data values (n) and a corresponding relative occurrence frequency ($F_k$) for each unique data value ($v_k$);
displaying a graph of frequency ($F_k$) versus data values ($v_k$) in each bin in a connected phase space; and
discarding data that has $[v_k-(N/n)]/\sigma_3 > z$, where the value of z is determined by solving $1/n = \frac{1}{2}\ \text{erfc}(z/>2)$, and $\sigma_3$ is a standard deviation in the occurrence frequency.

9. The method of claim 1, with an alternative embodiment for event forewarning, comprising determining a sequence of renormalized phase space dissimilarity measures from data sets for the test subject or process; summing said renormalized measures into a composite measure, $C_i$, for an i-th data set; performing a least-squares analysis over a window of m points of the said composite measure to obtain a straight line, $y_i = ai+b$, that best fits said composite data in a least-squares sense; determining a variance, $\sigma_1^2 = \Sigma_i (y_i - C_i)^2/(m-1)$, of said composite measure with respect to the straight line fit; obtaining a variability of the sequel window of m sequential points via the statistic, $G = \Sigma_i (y_i - C_i)^2/\Sigma_1^2$; comparing said value of G to a running maximum value of the same statistic, $G_{max}$; determining the forewarning of or failure onset of a critical event (such as a machine failure), when G is significantly more than $G_{max}$; obtaining a ratio, $R = (G_{max})_k/(G_{max})_{k-1}$, of the present and previous running maximum in G; and determining the forewarning of a critical event when R is significantly more than some limit.

10. A method for processing data to provide a forewarning of a critical event, comprising:
acquiring a plurality of sets of data for at least two channels of data from monitoring at least one physical test subject or physical process;
producing a set of multi-channel data representing a combination of said at least two channels of data;
computing a multi-channel time-delay phase-space (PS) construction, which has a form: $y(i)=[s(1)_1, s(1)_{1+\lambda}, s(1)_{i+2\lambda}, \ldots, s(2), s(2)_{i+\lambda}, s(2)_{i+2\lambda}, \ldots, s(c)_i, s(c)_{i+\lambda}, s(c)_{i+2\lambda}, \ldots]$, where s(c) denotes symbolized data for a c-th channel;
computing a renormalized measure of dissimilarity from distribution functions derived from a phase space for the multi-channel data;
comparing said renormalized measure of dissimilarity to a threshold ($U_C$) for a number of occurrences ($N_{OCC}$) to indicate a condition change in said renormalized measure of dissimilarity; and
detecting a simultaneous condition change in a plurality ($N_{SIM}$) of renormalized measures of dissimilarity to determine a forewarning of the critical event; and
providing an output of at least one of a graph, a table of data or an observable signal by which a human observer can detect the forewarning of the critical event.

11. The method of claim 10, further comprising:
performing a first filtering of each set of data with a zero-phase quadratic filter that filters out high-frequency artifacts; and
performing a second filtering of each set of data with a zero-phase quadratic filter to filter out low-frequency artifacts.

12. The method of claim 10, using an alternative embodiment for event forewarning, comprising determining a sequence of renormalized phase space dissimilarity measures from data sets collected during increasingly severe fault conditions; summing said renormalized measures into a composite measure, $C_1$, for an i-th data set; performing a least-squares analysis over a window of m points of the said composite measure to obtain a straight line, $y_i = ai+b$, that best fits said composite data in a least-squares sense; determining a variance, $\sigma_1^2 = \Sigma_i(y_i - C_i)^2/(m-1)$, of said composite measure with respect to the straight line fit; obtaining a variability of a sequel window of m sequential points via the statistic, $G = \Sigma_i(y_i - C_i)^2/\sigma_1^2$; comparing said value of G to a running maximum value of the same statistic, $G_{max}$; and determining an onset of a critical event, such as forewarning of a machine failure, when G is significantly more than G(non-end-of-life), or when R is significantly more than R(non-end-of-life), or detection of failure onset when G is significantly greater than G(end-of-life).

13. The method of claim 10, wherein the test subject is a human patient.

14. The method of claim 10, wherein the test subject is a mechanical device or physical process.

15. The method of claim 10, further comprising:
sorting the data values into ascending order from a minimum to a maximum;
determining a number of unique data values (n) and a corresponding relative occurrence frequency ($F_k$) for each unique data value ($v_k$);
displaying a graph of frequency ($F_k$) versus data values ($v_k$) in each bin in a connected phase space; and
discarding data that has $[v_k - (N/n)]/\sigma_3 > z$, where the value of z is determined by solving $1/n = \frac{1}{2}\ \text{erfc}(z/\sqrt{2})$, and $\sigma_3$ is the standard deviation in the occurrence frequency.

16. The method of claim 10, wherein the multi-channel time-delay phase-space (PS) construction is constructed from process-indicative data, which is three-phase electrical power data.

17. The method of claim 10, wherein the multi-channel time-delay phase-space (PS) construction is constructed from process-indicative data, which is vibration mechanical power data.

18. The method of claim 10, wherein the multi-channel time-delay phase-space (PS) construction is constructed from process-indicative data representing a difference between the two channels of data, which is EEG data.

* * * * *